(12) United States Patent
Chen et al.

(10) Patent No.: US 9,636,342 B2
(45) Date of Patent: May 2, 2017

(54) METHOD FOR TREATING PROSTATE CANCER

(71) Applicant: UNIVERSITY OF SOUTH CAROLINA, Columbia, SC (US)

(72) Inventors: Mengqian Chen, Columbia, SC (US); Igor Roninson, Lexington, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/439,127

(22) PCT Filed: Nov. 1, 2013

(86) PCT No.: PCT/US2013/067990
§ 371 (c)(1),
(2) Date: Apr. 28, 2015

(87) PCT Pub. No.: WO2014/071143
PCT Pub. Date: May 8, 2014

(65) Prior Publication Data
US 2015/0272953 A1    Oct. 1, 2015

Related U.S. Application Data

(60) Provisional application No. 61/721,134, filed on Nov. 1, 2012.

(51) Int. Cl.
*A61K 31/517*        (2006.01)
*A61K 31/5377*       (2006.01)

(52) U.S. Cl.
CPC ........ *A61K 31/517* (2013.01); *A61K 31/5377* (2013.01)

(58) Field of Classification Search
None
See application file for complete search history.

(56) References Cited

U.S. PATENT DOCUMENTS

2006/0235034 A1* 10/2006 Neamati ............... C07C 243/32
514/267

OTHER PUBLICATIONS

Haas, Michel J. CDK8 inhibitor: Senex's best thing. SciBX: Science-Business eXchange. 5(33), Aug. 23, 2012, p. 1-3.*
Schmidt, Lucy J. Gene Expression in Prostate Cancer Cells Treated With the Dual 5-Alpha-Reductase Inhibitor Dutasteride. Journal of Andrology. 25(6), (2004), 944-953.*

* cited by examiner

*Primary Examiner* — Samantha Shterengarts
(74) *Attorney, Agent, or Firm* — Wayne A. Keown; Verrill Dana LLP

(57) ABSTRACT

The invention provides a method for treating prostate cancer in a subject comprising administering to the subject an effective amount of a selective inhibitor of one or more of CDK8 and CDK19. In some embodiments the inhibitor inhibits CDK19. In some embodiments, the inhibitor inhibits CDK8 at a Kd of lower than 200 nM and/or inhibits CDK19 at a Kd of lower than 100 nM. In some embodiments, the prostate cancer is androgen independent. In some embodiments, the prostate cancer is androgen independent due to one or more of androgen receptor gene amplification, androgen receptor gene mutation, ligand-independent transactivation of androgen receptor and activation of intracellular androgen synthesis. In some embodiments, the inhibitor inhibits increased activity of NF-κB. In some embodiments, the inhibitor does not inhibit increased basal levels of NF-κB. In some embodiments, inhibition of one or more genes by AR is not inhibited.

6 Claims, 16 Drawing Sheets

METHOD FOR TREATING PROSTATE CANCER

BACKGROUND OF THE INVENTION

Field of the Invention

The invention relates to the treatment of cancer. More particularly, the invention relates to the treatment of prostate cancer.

Summary of the Related Art

As the most common malignancy in US males, prostate cancer remains a challenging disease. In contrast to other human cancers, it is exquisitely dependent on androgenic steroids that exert their biological effects through the androgen receptor (AR)[1, 2].

The classical model for AR activation involves a conformational change induced by ligand binding, enhanced nuclear translocation, and binding to the androgen-responsive elements in the proximal promoters or distal enhancers of target genes to regulate transcription[3]. AR-regulated genes are essential for prostate tumor cell growth, invasion and metastasis[2, 3]. More importantly, recent studies indicate that AR binding dynamics to chromatin vary in prostate cancer cells, depending on cellular context, producing different effects on gene expression in different cases[4-6]. Therefore, it is critically important to fully understand the molecular mechanisms of AR-mediated transcription, especially those that can be targeted by new drugs.

The first line treatments for patients with advanced prostate cancer are androgen-deprivation therapies that suppress the AR signaling by either inhibiting the androgen-synthetic pathway or antagonizing AR function[2]. Despite strong responses to androgen-deprivation therapies, patients often relapse with a more aggressive, therapy-resistant form of the disease referred to as castration refractory prostate cancer (CRPC)[7, 8]. Recent studies showed that most of CRPC tumor cells continue to utilize their endogenous androgen signaling system to drive their growth through restoration of AR function[9-11]. The mechanisms of AR reactivation include AR gene amplification, ligand-independent transactivation of AR, or activation of intracellular androgen synthesis[12-14]. Novel anti-androgen therapeutic agents are being developed to treat CRPC, including a new potent testosterone-synthesis inhibitor (abiraterone)[15, 16] and a high-affinity anti-AR drug (MDV-3100, a.k.a. enzalutamide)[17, 18]. Although clinical studies showed that these drugs confer survival advantage[13, 19-21], the CRPC still remains far from being cured and requires new effective treatments after the acquisition of resistance to these drugs. All the existing methods for blocking androgen signaling rely on inhibiting the production of the ligand or the ligand-receptor association, which can be overcome in cancers by multiple mechanisms of AR reactivation. Several novel anti-AR drugs have recently been developed to block the AR signaling by inducing AR protein degradation[22-24]. Recent studies have indicated, however, that AR not only induces certain cancer-promoting genes but also represses other genes that are involved in androgen synthesis, DNA synthesis and proliferation[25]. Activation of the latter genes by blocking all the effects of AR or by inducing AR degradation may stimulate the transition of PCa cells from an androgen-dependent (AD) to an androgen-independent (AI) state.

There is therefore, a need to develop a strategy targeting other molecules that potentiate AR-mediated transcription to block the hyperactive androgen signaling and to extend the effectiveness of hormone therapies in prostate cancer patients. In particular, there is a need to develop a strategy for inhibiting AR-mediated induction of transcription but not the repression of transcription by AR.

BRIEF SUMMARY OF THE INVENTION

The invention provides a new strategy targeting other molecules that potentiate AR-mediated transcription to block the hyperactive androgen signaling and to extend the effectiveness of hormone therapies in prostate cancer patients. The instant inventors have surprisingly discovered a novel method for inhibition of AR signaling that functions independently of ligand-AR interaction, and which is based on the inhibition of two closely related transcription-regulating serine/threonine kinases, CDK8 and CDK19.

In contrast to better-known members of the CDK family[26], the closely related CDK8 and CDK19 regulate transcription but not cell cycle progression, and their depletion does not inhibit the growth of normal cells[27] or many tumor cells[28, 29]. CDK8 and CDK19 are the two isoforms of a component of the transcription-regulating Mediator complex[30] but can also act outside of the Mediator[31, 32]. Early studies depicted CDK8 as a transcriptional co-repressor based on its negative regulation of the general transcription initiation factor IIH[33] and a group of transcriptional activators[34]. However, a series of recent reports demonstrated that CDK8 serves as a positive transcription regulator in multiple signaling pathways with biomedical relevance, including the p53 pathway[35], Wnt/β-catenin pathway[36], the serum response network[28], the TGFβ signaling pathway[35], as well as Thyroid hormone Receptor[37] and Sterol-Regulatory Element Binding Protein[38]-dependent transcription. In regard to cancer, CDK8 has been recognized as an oncogene in melanoma and colorectal cancers[36, 39] and it was recently implicated in the cancer stem cell phenotype[40]. In contrast to CDK8, its vertebrate paralog CDK19 has been poorly studied because it is not expressed as highly as CDK8 in most tissues. However, CDK19 is expressed in normal prostate[41]. High CDK8 and CDK19 expression levels were also found to be predictive markers of poor relapse-free survival in breast cancers and in platinum-treated ovarian cancers[29]. Furthermore, CDK8 was shown to be a mediator of damage-induced tumor-promoting paracrine activities of normal tissues, colon carcinoma and fibrosarcoma cells[29]. However, there was no prior evidence linking CDK8 or CDK19 with AR activity or androgen-independent growth of prostate cancers.

The invention provides a method for treating prostate cancer in a subject comprising administering to the subject an effective amount of a selective inhibitor of one or more of CDK8 and CDK19. In some embodiments the inhibitor inhibits CDK19. In some embodiments, the inhibitor inhibits CDK8 at a Kd of lower than 200 nM and/or inhibits CDK19 at a Kd of lower than 100 nM.

In some embodiments, the prostate cancer is androgen independent. In some embodiments, the prostate cancer is androgen independent due to one or more of androgen receptor gene amplification, androgen receptor gene mutation, ligand-independent transactivation of androgen receptor and activation of intracellular androgen synthesis.

In some embodiments, the inhibitor inhibits increased activity of NF-κB. In some embodiments, the inhibitor does not inhibit increased basal levels of NF-κB.

DETAILED DESCRIPTION OF THE PREFERRED EMBODIMENTS

Figure 1A:
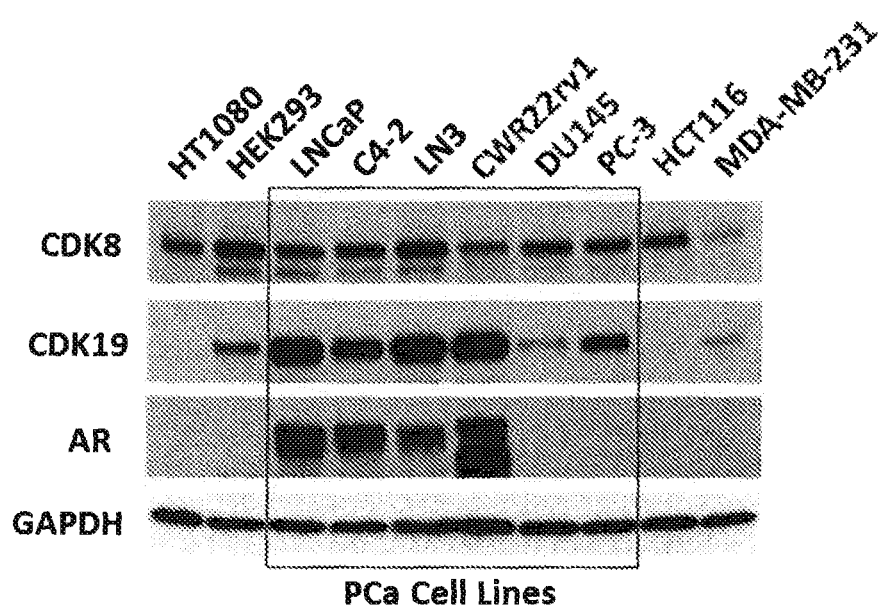
FIG. 1A shows that CDK19 protein is expressed at higher levels in AR-positive (LNCaP, LN3, C42, CWR22rv1) prostate cancer cells compared to AR-negative (DU145 and PC3) prostate cancer cell lines, or to fibrosarcoma (HT1080), human embryonic kidney (HEK293) and colon carcinoma (HCT116) cells.

The invention provides a method for treating prostate cancer in a subject comprising administering to the subject an effective amount of a selective inhibitor of one or more of CDK8 and CDK19. In some embodiments the inhibitor inhibits CDK19. In some embodiments, the inhibitor inhibits CDK8 at a Kd of lower than 200 nM and/or inhibits CDK19 at a Kd of lower than 100 nM. For purposes of the invention, "specific inhibitors of CDK8/19" are small molecule compounds that inhibit CDK8 or CDK8 and CDK19 to a greater extent than they inhibit certain other CDKs. In some embodiments, such compounds further inhibit CDK8 to a greater extent than CDK9. In preferred embodiments, such greater extent is at least 2-fold more than CDK9. Compounds that are useful in the invention are described in co-pending US Patent Publications 20120071477 and 20120071477 and PCT Publication WO2013/116786. Extent of inhibition is measured by the assays taught in co-pending PCT Publication WO2013/116786.

In some embodiments, the prostate cancer is androgen independent. In some embodiments, the prostate cancer is androgen independent due to one or more of androgen receptor gene amplification, androgen receptor gene mutation, ligand-independent transactivation of androgen receptor and activation of intracellular androgen synthesis.

In some embodiments, the inhibitor inhibits induced activity of NF-κB. In some embodiments, the inhibitor does not inhibit increased basal levels of NF-κB. The term "induced NFκB transcriptional activity" means that the transcriptional function performed by NFκB is performed at greater than basal NFκB transcriptional activity level. The term "basal NFκB transcriptional activity" means the level of transcriptional function performed by NFκB in a cell under normal conditions, i.e., in the absence of the disease or disorder. In some embodiments, the amount of active NFκB in the nucleus of the cells is not increased, but rather only the level of NFκB activity is increased.

The term "treating" means reducing or eliminating at least some of the signs or symptoms of the disease. The term "subject" includes a human. The terms "administering", "administration" and the like are further discussed below.

In some embodiments, a compound according to the invention is administered as a pharmaceutical formulation including a physiologically acceptable carrier. The term "physiologically acceptable" generally refers to a material that does not interfere with the effectiveness of the compound and that is compatible with the health of the subject. The term "carrier" encompasses any excipient, diluent, filler, salt, buffer, stabilizer, solubilizer, oil, lipid, lipid containing vesicle, microspheres, liposomal encapsulation, or other material well known in the art for use in physiologically acceptable formulations. It will be understood that the characteristics of the carrier, excipient, or diluent will depend on the route of administration for a particular application. The preparation of physiologically acceptable formulations containing these materials is described in, e.g., Remington's Pharmaceutical Sciences, 18th Edition, ed. A. Gennaro, Mack Publishing Co., Easton, Pa., 1990. The active compound is included in the physiologically acceptable carrier or diluent in an amount sufficient to deliver to a patient a prophylactically or therapeutically effective amount without causing serious toxic effects in the patient treated. The term an "effective amount" or a "sufficient amount" generally refers to an amount sufficient to affect a reduction or elimination of at least one symptom or sign of the disease or disorder.

In the methods according to the invention, administration of a compound according to the invention can be by any suitable route, including, without limitation, parenteral, oral, intratumoral, sublingual, transdermal, topical, intranasal, aerosol, intraocular, intratracheal, intrarectal, mucosal, vaginal, by dermal patch or in eye drop or mouthwash form. Administration of the compound or pharmaceutical formulation can be carried out using known procedures at dosages and for periods of time effective to reduce symptoms or surrogate markers of the disease.

The following examples are intended to further illustrate certain embodiments supporting the invention and are not intended to limit the scope of the invention.

EXAMPLE 1

CDK8 and CDK19 Expression in Prostate Cancer

FIG. 1A shows immunoblotting of CDK8, CDK19, AR and GAPDH (normalization standard) in HT1080 (fibrosarcoma), HEK-293 (embryonic kidney), MDA-MB-231 (breast carcinoma), HCT116 (colon carcinoma) and prostate cancer cell lines LNCaP (androgen-dependent), androgen-independent LNCaP derivatives C4-2 and LN3 and androgen-independent prostate cancer cell lines CWR22rv1, DU145 and PC-3. The following primary antibodies were used for immunoblotting: goat-anti-CDK8 (Santa Cruz, sc-1521), rabbit-anti-CDK19 (Sigma, HPA007053), rabbit-anti-AR (Santa Cruz, sc-13062) and mouse-anti-GAPDH (Santa Cruz, sc-32233). While CDK8 shows similar expression levels in all the cell lines, with significantly lower expression only in MDA-MB-231, CDK19 is almost undetectable in HT1080 and HCT116 cells but is expressed in all the prostate cancer lines that express AR.

Figure 1B:
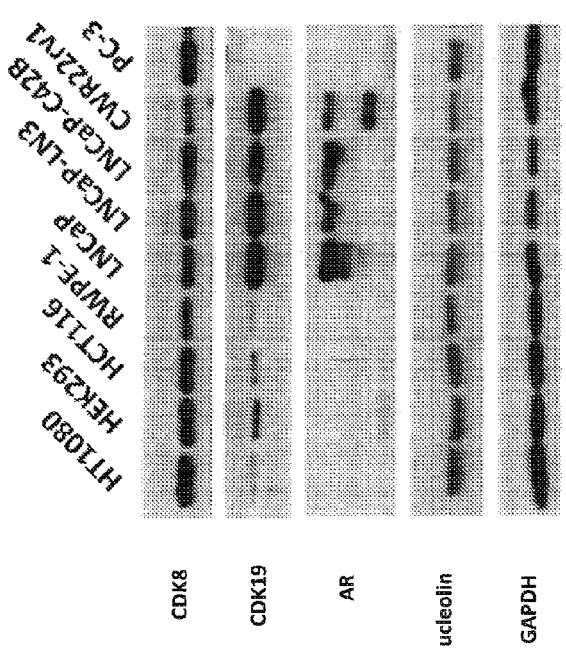
FIG. 1B shows that CDK19 protein is expressed at higher levels in in AR-positive (LNCaP, LN3, C42, CWR22rv1) prostate cancer cells compared to AR-negative (PC3) prostate cancer cells, non-malignant prostate epithelial cells (RWPE-1), fibrosarcoma (HT1080), human embryonic kidney (HEK293) and colon carcinoma (HCT116) cells.

FIG. 1B shows immunoblotting of CDK8, CDK19, AR, nucleolin and GAPDH (the two latter are normalization standards) in HT1080 (fibrosarcoma), HEK-293 (embryonic kidney), HCT116 (colon carcinoma), RWPE-1 (immortal but untransformed prostate epithelial cells) and prostate cancer cell lines LNCaP (androgen-dependent), androgen-independent LNCaP derivatives C4-2 and LN3 and androgen-independent prostate cancer cell lines CWR22rv1 and PC-3. While CDK8 shows similar expression levels in all the cell lines, CDK19 is strongly overexpressed in those prostate cancer lines that express AR relative to all the other cell lines. Hence, elevated CDK19 expression is associated with AR-expressing prostate cancer cells.

Figure 1C:
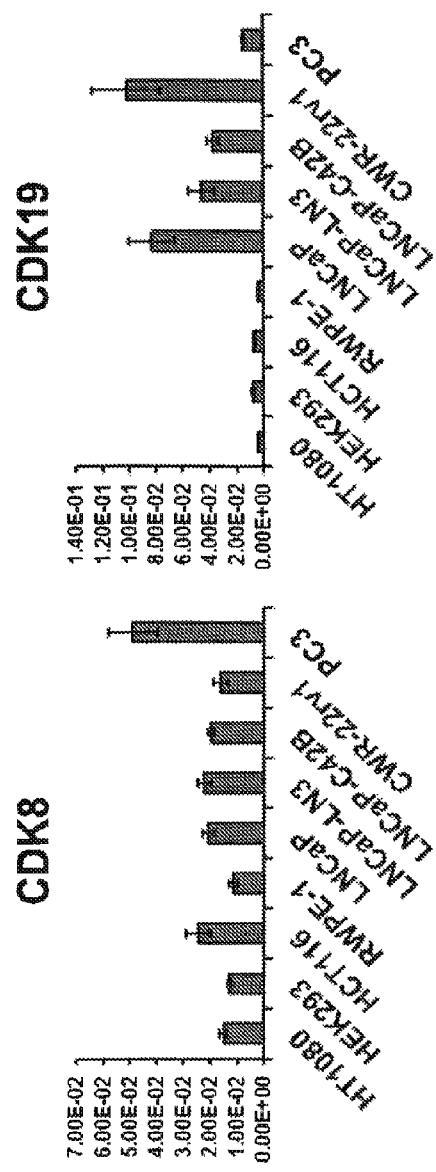
FIG. 1C shows that CDK19 RNA is expressed at higher levels in in AR-positive (LNCaP, LN3, C42, CWR22rv1) prostate cancer cells compared to AR-negative (PC3) prostate cancer cells, non-malignant prostate epithelial cells (RWPE-1), fibrosarcoma (HT1080), human embryonic kidney (HEK293) and colon carcinoma (HCT116) cells.

FIG. 1C shows qPCR analysis of mRNA expression of CDK8 and CDK19 in the same cell lines that were used for immunoblotting analysis in FIG. 1B. The qPCR results agree with the results of immunoblotting, with CDK8 showing similar RNA expression in all the cell lines (with the highest levels observed in PC3 cells), whereas CDK19 shows much higher RNA expression in AR-expressing prostate cancer cells than in any other cell lines.

Figure 1D:
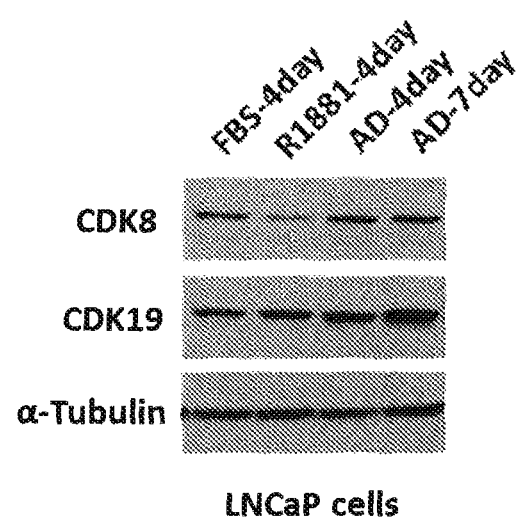
FIG. 1D shows that androgen treatment down-regulates CDK8 protein, whereas androgen depletion up-regulates CDK19 and CDK8 protein expression in LNCaP cells.

FIG. 1D shows the expression of CDK8, CDK19 and α-tubulin (normalization standard, Sigma, T5168) in androgen-dependent LNCaP cells cultured in complete media supplemented with fetal bovine serum (FBS) or in charcoal-stripped serum (CSS) media (androgen-deprived, AD) or in CSS media supplemented with 100 pM androgen agonist R1881 (also known as methyltrienolone) for the indicated number of days. This analysis shows that androgen treatment downregulates CDK8 whereas androgen deprivation up-regulates CDK8 and CDK19 proteins in LNCaP cells (FIG. 1D), indicating that CDK8 and CDK19 expression is regulated via AR.

EXAMPLE 2

Effects of CDK8/19 Inhibitors on AR Activity

To test the role of CDK8/19 in AR activity, we have used selective small-molecule inhibitors of CDK8/19 developed by Senex Biotechnology, Inc. (Senex) and termed Senexin A (a.k.a. SNX2-1-53) and Senexin B (a.k.a. SNX2-1-165). Senexin A has been described in a recent article[29] and Senexin B in PCT Publication WO2013/116786. These small molecules selectively bind to the ATP pockets of CDK8/19 to inhibit their kinase activity. Senexin B inhibits CDK8/19 kinase activity at lower Kd (140 nM for CDK8 and 80 nM for CDK19) and possesses higher water solubility (as high as 50 mM) compared to Senexin A.

Figure 2A:
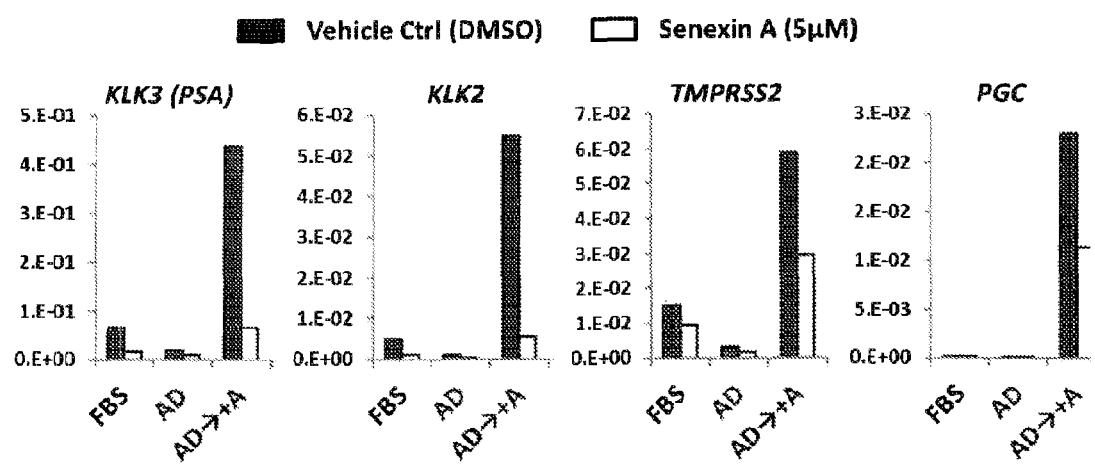
FIG. 2A shows that treatment of androgen-dependent LNCaP cells with Senexin A significantly inhibits androgen-stimulated transcriptional activation of several androgen-responsive genes such as PSA (KLK3), KLK2, TMPRSS2 and PGC under either androgen-supplemented or androgen-deprived conditions.

The effects of Senexin A (5 µM) on the expression of the indicated androgen-responsive genes in LNCaP cells cultured in normal culture media for 3d (FBS) or in androgen-deprived (CSS) media for 5d (AD, androgen deprivation) or in androgen-supplemented media (500 pM R1881) for 24 hr after 5-day androgen-deprivation (AD→+A) were evaluated. Treatment of androgen-dependent LNCaP cells with Senexin A significantly inhibited androgen-stimulated transcriptional activation of several androgen-responsive genes such as PSA (KLK3), KLK2, TMPRSS2 and PGC under either androgen-supplemented or androgen-deprived conditions (FIG. 2A).

Figures 2B, 2C:
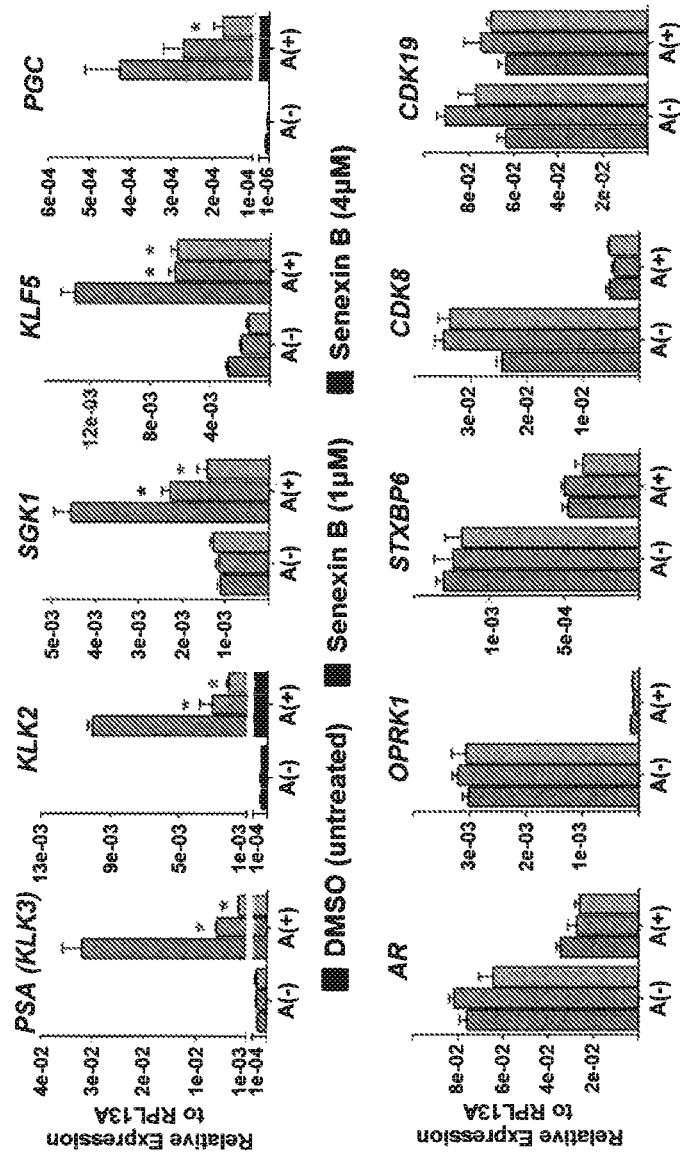
FIG. 2B shows that treatment of androgen-dependent LNCaP cells with Senexin B significantly inhibits androgen-stimulated transcriptional activation of several androgen-inducible genes such as PSA (KLK3), KLK2, SGK1, KLF5 and PGC under androgen-supplemented conditions.
FIG. 2C shows that treatment of androgen-dependent LNCaP cells with Senexin B does not interfere with the inhibition of several androgen-inhibited genes such as AR, OPRK1, STXBP6 and CDK8.

The effects of Senexin B (1 µM and 4 µM) on the expression of the indicated androgen-responsive genes in LNCaP cells cultured in androgen-deprived (CSS) media for 5d (A−) or in androgen-supplemented media (500 pM R1881) for 24 hr after 5-day androgen-deprivation (A+) were also evaluated. Treatment of androgen-dependent LNCaP cells with Senexin B significantly inhibited androgen-stimulated transcriptional activation of several androgen-responsive genes such as PSA (KLK3), KLK2, TMPRSS2, SGK1, KLF5 and PGC under androgen-supplemented conditions (FIG. 2B). On the other hand, treatment of the same cells with Senexin B did not interfere with the inhibition of several androgen-inhibited genes such as AR, OPRK1 or STXBP6 (FIG. 2C). Androgen addition also inhibited the expression of CDK8 (but not of CDK19), and Senexin B did not interfere with this inhibition (FIG. 2C). Hence, CDK8/19 inhibition has an especially beneficial effect of inhibiting only the induction but not the repression of gene expression by androgen.

The effect of Senexin B on the expression of androgen-responsive genes in LNCaP cells cultured in CSS media for 3d [R1881(−)] or in androgen-supplemented media (500 pM R1881) for 24 hr after 2-day androgen-deprivation [R1881 (+)] was measured. Senexin B was added 1 hr before R1881 treatment and maintained in culture until RNA sample collection. Gene expression was measured by qPCR, with housekeeping gene RPL13A as normalization standard (*: $p<0.05$ between Senexin B and DMSO). Pretreatment of androgen-deprived LNCaP cells by Senexin B significantly inhibited androgen-stimulated transcription of these genes (FIG. 3), suggesting that CDK8/19 positively regulate androgen signaling in prostate cancer cells.

Figure 4:
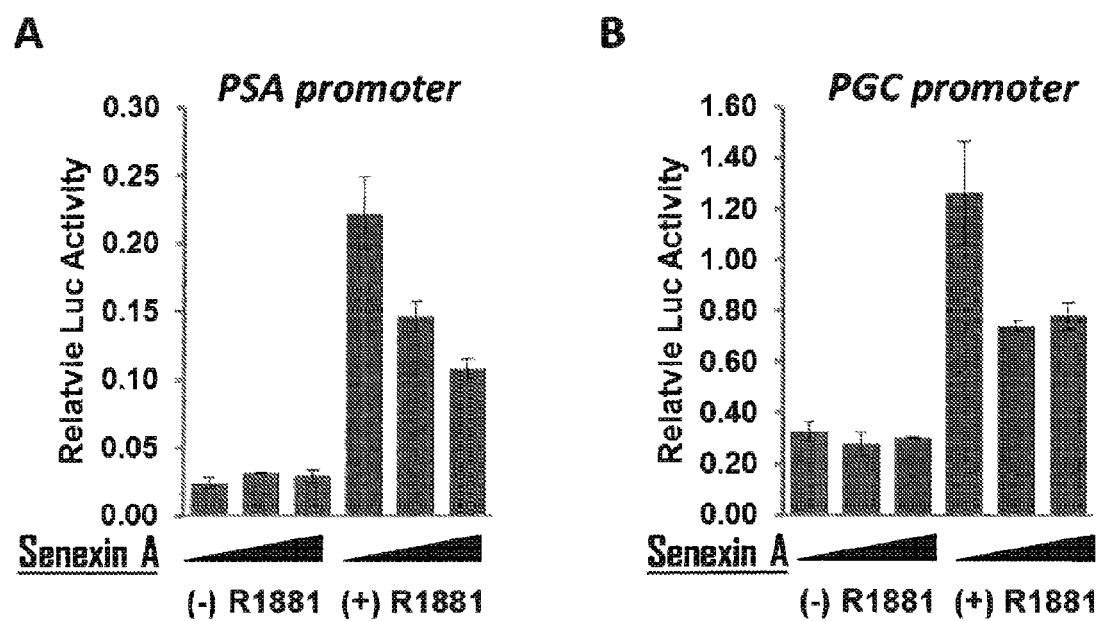
FIG. 4A shows that in HEK293 cells that express both CDK8 and CDK19 and overexpress full-length wild-type AR, Senexin A (1 µM and 5 µM) significantly inhibits the activation of an androgen-responsive construct (firefly luciferase reporter under PSA gene promoter) in the presence of R1881 but not in androgen-free media.
FIG. 4B shows that in HEK293 cells that express both CDK8 and CDK19 and overexpress full-length wild-type AR, Senexin A (1 µM and 5 µM) significantly inhibits the activation of another androgen-responsive construct (firefly luciferase reporter under PGC gene promoter) in the presence of R1881 but not in androgen-free media.
Figure 5:
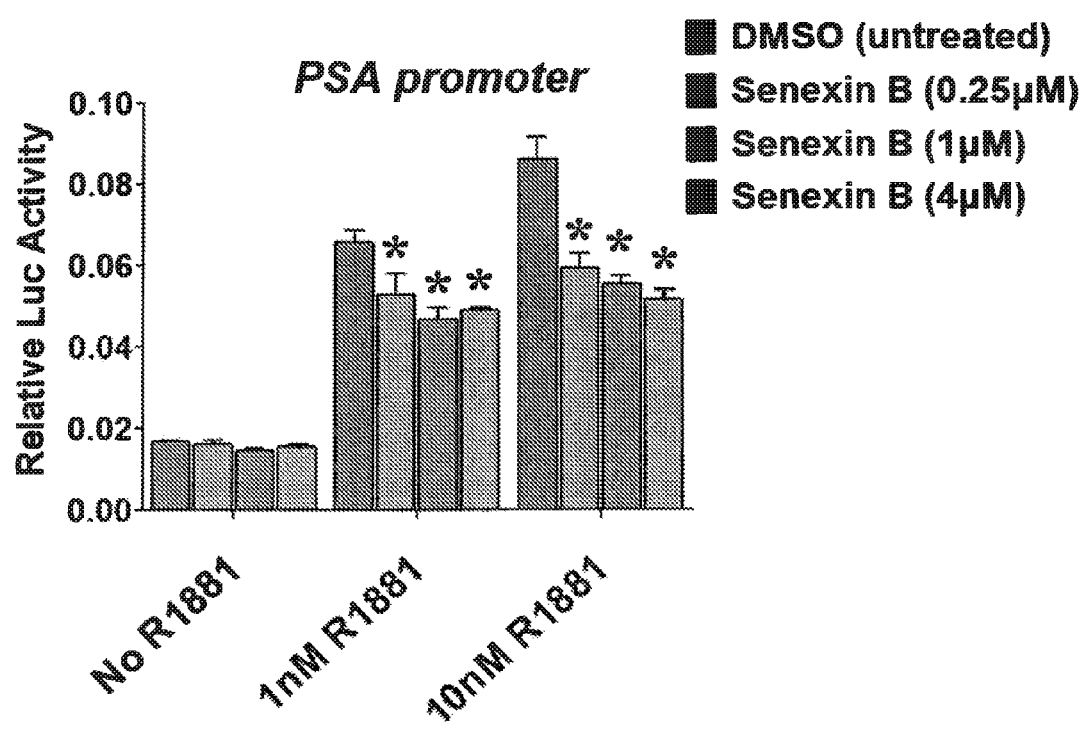
FIG. 5 shows that in HEK293 cells that express both CDK8 and CDK19 and overexpress full-length wild-type AR, Senexin B significantly inhibits the activation of an androgen-responsive construct (firefly luciferase reporter under PSA gene promoter) in the presence of R1881 but not in androgen-free media.

To confirm the role of CDK8/19 in AR activation, we analyzed the inhibitory effects of Senexin A and Senexin B by a promoter activity assay in HEK293 cells that express both CDK8 and CDK19 (FIG. 1A). When full-length wild-type AR was overexpressed in HEK-293 cells, either Senexin A or Senexin B significantly inhibited the activation of an androgen-responsive construct (firefly luciferase reporter under PSA gene promoter) in the presence of R1881 but not in androgen-free media (FIG. 4A and FIG. 5). Similar results were observed with another androgen-responsive promoter (PGC) (FIG. 4B). These results indicate that CDK8/19 positively regulates AR function.

EXAMPLE 3

Figure 6A:
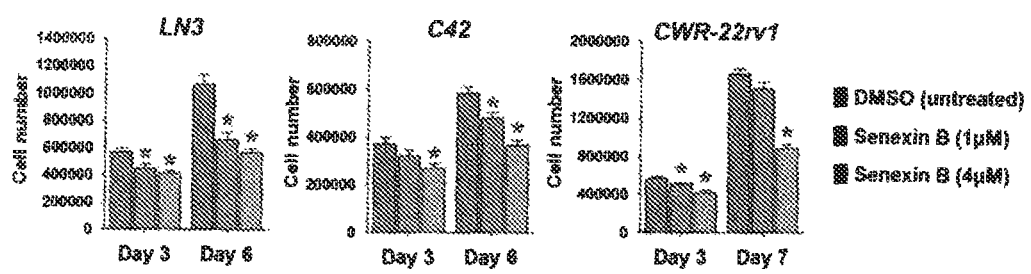
FIG. 6A shows that LNCaP derivatives LN3 and C4-2 and CWR22 derivative CWR22rv1 androgen-independent prostate cancer cells grow well under androgen-depleted conditions (in CSS media), but this androgen-independent growth was strongly inhibited by Senexin B.

Effects of CDK8/19 Inhibitors on Cell Growth and ARG Expression in Androgen-Independent Prostate Cancer Cells in Androgen-Depleted Media In most of CRPC patients, prostate cancer tumor cells restore their AR activities despite low-androgen environment or presence of AR antagonists. We tested whether a CDK8/19 inhibitor Senexin B inhibits androgen-independent growth in several androgen-independent prostate cancer cell lines that were derived from castration-relapse or metastatic xenografts of parental androgen-dependent prostate cancer cell lines, including LNCaP derivatives LN3 and C4-2 and CWR22 derivative CWR22rv1. The effect of Senexin B on the growth of AR-expressing androgen-independent prostate cancer cells in androgen-free media was measured. $2 \times 10^5$ prostate cancer cells were seeded in CSS media with different concentrations of Senexin B and cultured for the indicated number of days before the total cell number was counted (n=4). These androgen-independent prostate cancer cells grow well under androgen-depleted conditions (in CSS media), but this androgen-independent growth was strongly inhibited by Senexin B (FIG. 6A).

Figure 6B:
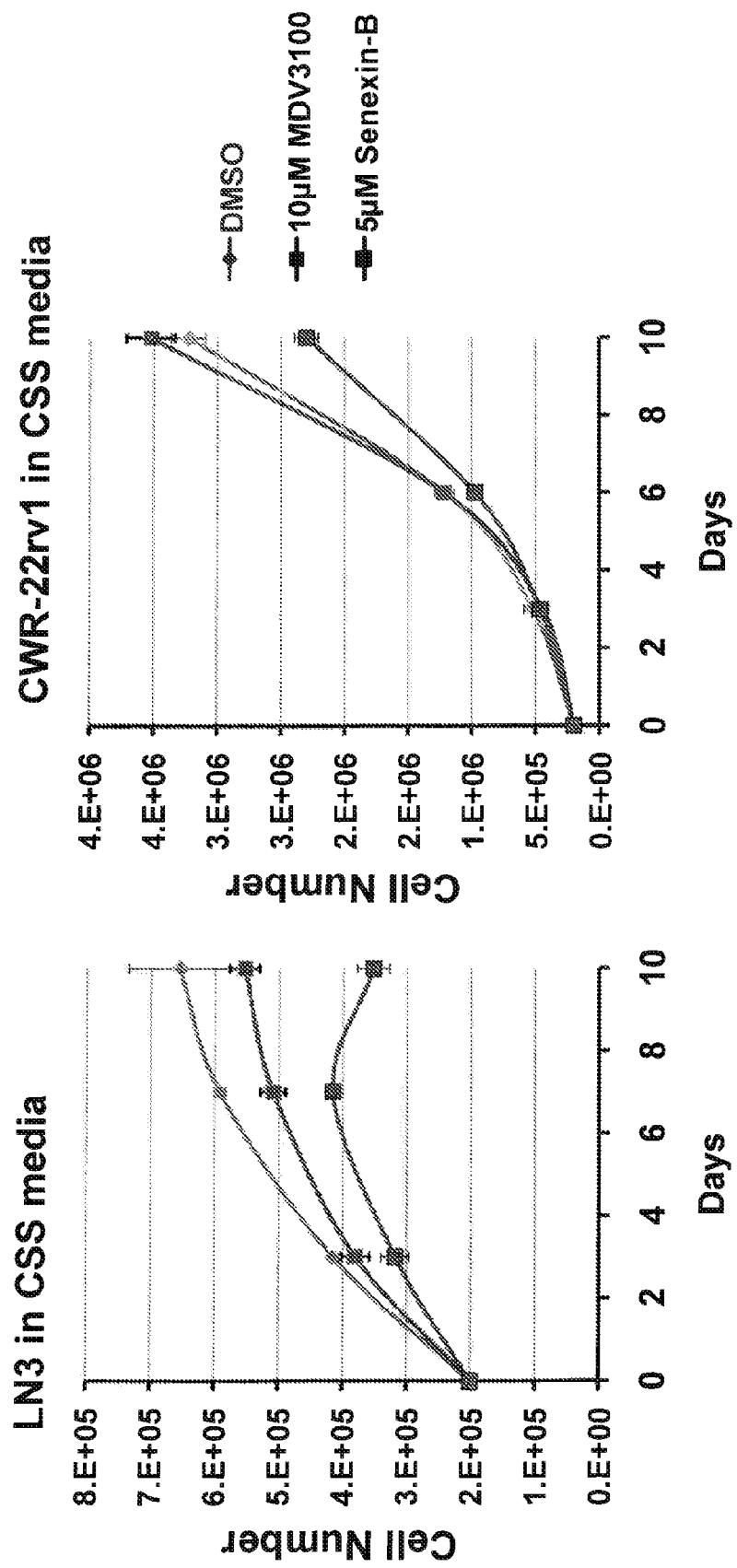
FIG. 6B shows that 5 µM Senexin B strongly inhibits the growth of LNCaP derivative LN3 and significantly inhibits the growth of CWR22 derivative CWR22rv1 androgen-independent prostate cancer cells under androgen-depleted conditions (in CSS media), and that 10 µM MDV3100 (enzalutamide) weakly inhibits the growth of LNCaP-LN3 cells and does not inhibit the growth of CWR22rv1 cells under the same androgen-depleted conditions.

We have also analyzed the growth of androgen-independent cell lines, LNCaP derivative LN3 and CWR22 derivative CWR22rv1, in CSS media, in the absence or in the presence of Senexin B or androgen antagonis MDV3100 (enzalutamide). $2 \times 10^5$ cells were seeded in CSS media with vehicle (DMSO) control, 5 μM Senexin B or 10 μM MDV3100 and cultured for indicated time before total cell number was counted (n=3). FIG. 6B shows that Senexin B strongly inhibited the growth of LNCaP-LN3 and significantly inhibited the growth of CWR22rv1 cells, whereas MDV3100 weakly inhibited the growth of LNCaP-LN3 cells and does not inhibit the growth of CWR22rv1 cells under the same androgen-depleted conditions.

Figure 6C:
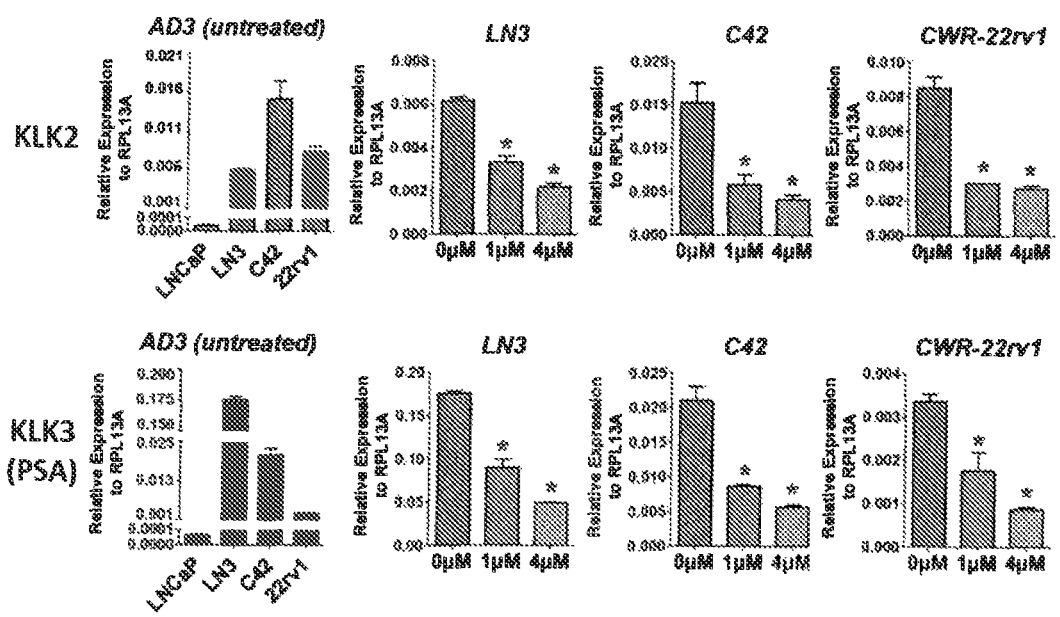
FIG. 6C shows that LNCaP derivatives LN3 and C4-2 and CWR22 derivative CWR22rv1 androgen-independent prostate cancer cells highly express AR-dependent genes, PSA and KLK2 compared to the androgen-dependent parental LNCaP cells after 3-day androgen deprivation (AD3), and that Senexin B down-regulates the expression of PSA and KLK2 in all three androgen-independent-prostate cancer cell lines grown in the absence of androgen.

Endogenous AR activities in these cells were estimated by qPCR analysis of mRNA expression of AR-dependent genes, KLK3 (PSA) and KLK2. The effect of Senexin B on the expression of KLK2 and KLK3 (PSA) in androgen-independent prostate cancer cells was measured. FIG. 6C shows basal gene expression in LNCaP and androgen-independent prostate cancer cell lines under 3-day androgen-deprivation conditions (AD3), and gene expression in cells cultured in CSS media (2d) and treated with Senexin B or vehicle control for 24 hours. *: $p<0.05$ between Senexin B and DMSO.

Figure 3:
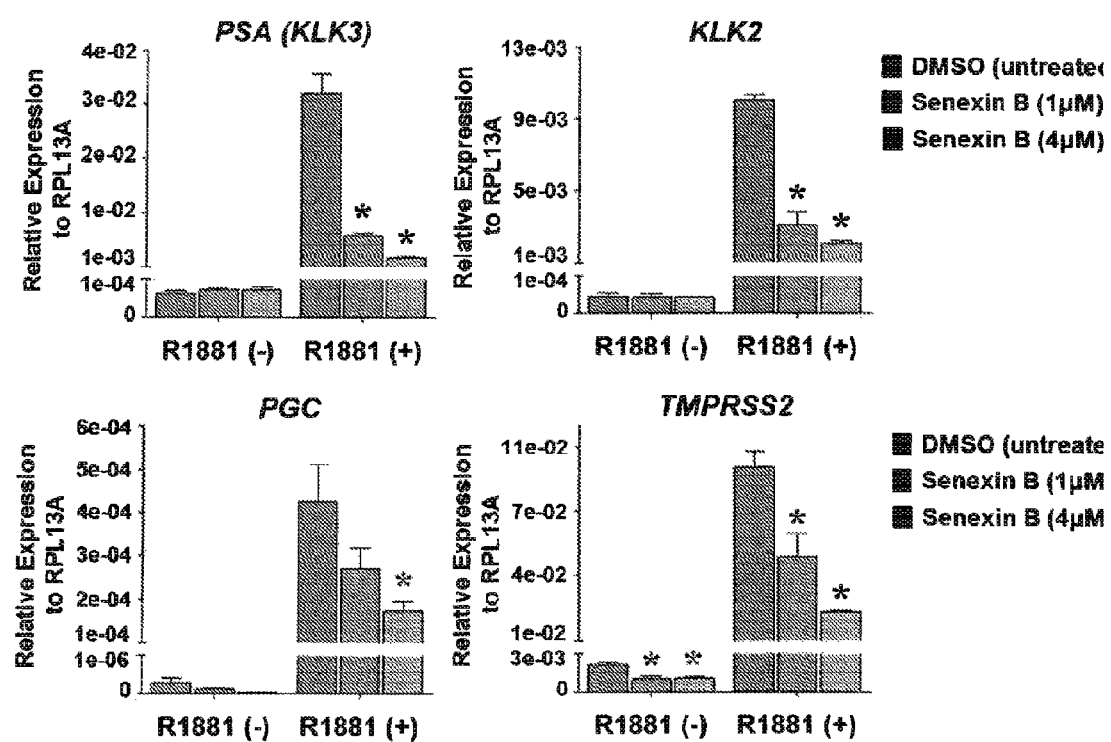
FIG. 3 shows that pretreatment of androgen-deprived LNCaP cells by Senexin B (at 1 µM and 4 µM) for one hour significantly inhibits androgen-stimulated transcription of several androgen-responsive genes such as PSA (KLK3), KLK2, TMPRSS2 and PGC.
Figure 6D:
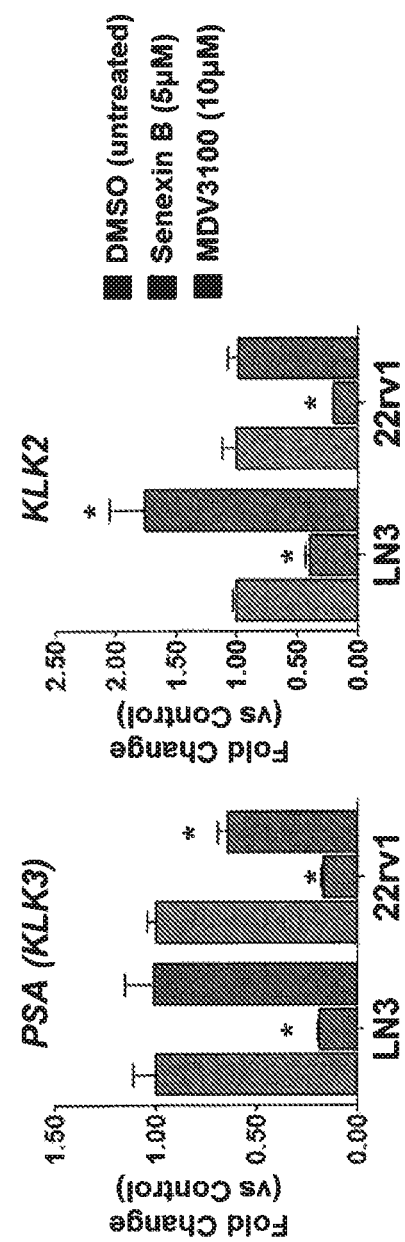
FIG. 6D shows that 5 µM Senexin B strongly down-regulates the expression of PSA and KLK2 in LNCaP-LN3 and CWR22rv1 androgen-independent-prostate cancer cell lines grown in the absence of androgen, whereas 10 µM MDV3100 (enzalutamide) weakly down-regulates the expression of PSA and does not down-regulate the expression of KLK2 in LNCaP-LN3 cells and does not down-regulate the expression of either PSA or KLK2 in CWR22rv1 cells under the same androgen-depleted conditions.

All three androgen-independent prostate cancer cell lines showed much higher expression of these genes compared to the androgen-dependent parental LNCaP cells after 3-day androgen deprivation (AD3, FIG. 6C). Strikingly, Senexin B down-regulated the expression of PSA and KLK2 in all three androgen-independent-prostate cancer cell lines grown in the absence of androgen (FIG. 6C) as effectively as it inhibits androgen-stimulated PSA/KLK2 expression in LNCaP cells (FIG. 3). FIG. 6D compares the effects of 5 μM Senexin B and 10 μM MDV3100 (enzalutamide) on the expression of PSA and KLK2 in LNCaP-LN3 and CWR22rv1 cells grown in the absence of androgen. Senexin B strongly down-regulates PSA and KLK2 expression in both androgen-independent-prostate cancer cell lines, whereas MDV3100 weakly down-regulates the expression of PSA and does not down-regulate the expression of KLK2 in LNCaP-LN3 cells and does not down-regulate the expression of either PSA or KLK2 in CWR22rv1 cells under the same androgen-depleted conditions.

These results suggest that Senexin B suppresses ligand-independent AR signaling in androgen-independent prostate cancer cells, which is required by these cells to proliferate in a low-androgen environment. The observation that Senexin B is able to inhibit cell growth and downregulate expression of androgen-regulated genes in CWR22rv1 cells is of special interest since constitutive androgen signaling in this cell line is rendered by a truncated AR[42]. This truncated form is resistant to current anti-androgen drugs designed for targeting the ligand-binding domain of AR because the C-terminal truncation deletes the ligand-binding domain and makes it ligand-independent. Hence CDK8/19 may also play an important role in active transcription mediated by activated ARs (full-length, mutated or truncated) in androgen-independent-prostate cancer cells.

Figure 7:
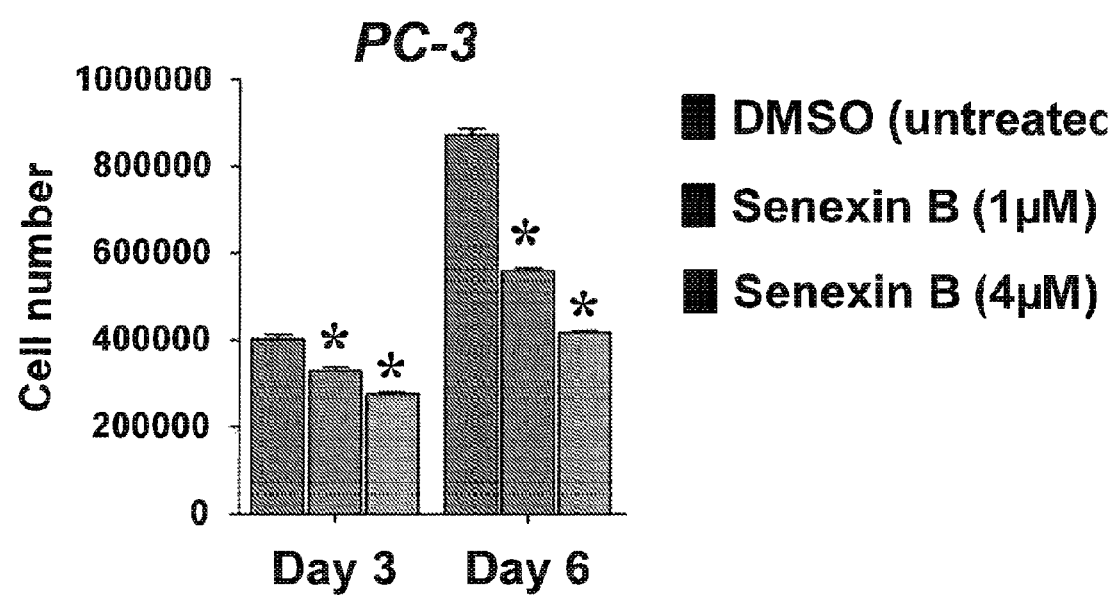
FIG. 7 shows that the growth of PC-3 cells in androgen-depleted CSS media is inhibited by Senexin B.

We have also tested if Senexin B inhibits the growth of an androgen-independent-prostate cancer cell line PC-3, which does not express AR (FIG. 1A), and which has developed the androgen-independent phenotype through an AR-independent mechanism. PC-3 cell growth was previously shown to be inhibited by the inhibition of transcription factor NFκB[43-45], and CDK8/19 inhibition was discovered by Senex to decrease the induction of NFκB transcriptional activity (PCT Publication WO2013/040153). The effect of Senexin B on PC-3 prostate cancer cell growth in androgen-free media was measured. $2 \times 10^5$ PC-3 cells were seeded in CSS media with different concentrations of Senexin B and cultured for the indicated number of days before the total cell number was counted (n=4). *: $p<0.05$ between Senexin B and DMSO. As shown in FIG. 7, the growth of PC-3 cells in androgen-depleted CSS media was inhibited by Senexin B. Hence, CDK8/19 inhibition inhibits the androgen-independent growth of androgen-independent prostate cancer cells that have developed androgen independence through different mechanisms.

EXAMPLE 4

Figure 8:
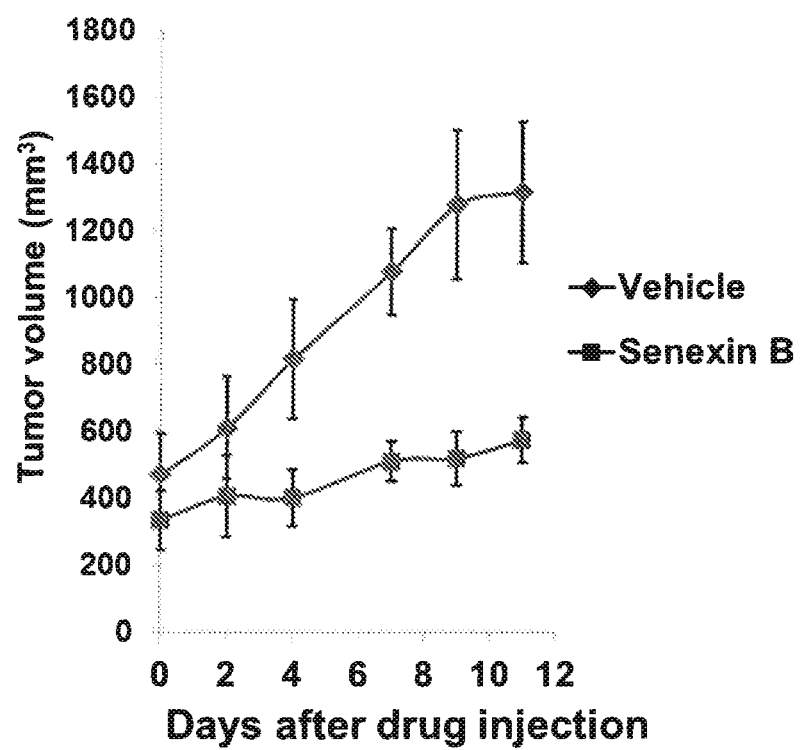
FIG. 8 shows effects of Senexin B treatment on the tumor volume growth curve of LN3 xenografts in nude mice.
Figure 9:
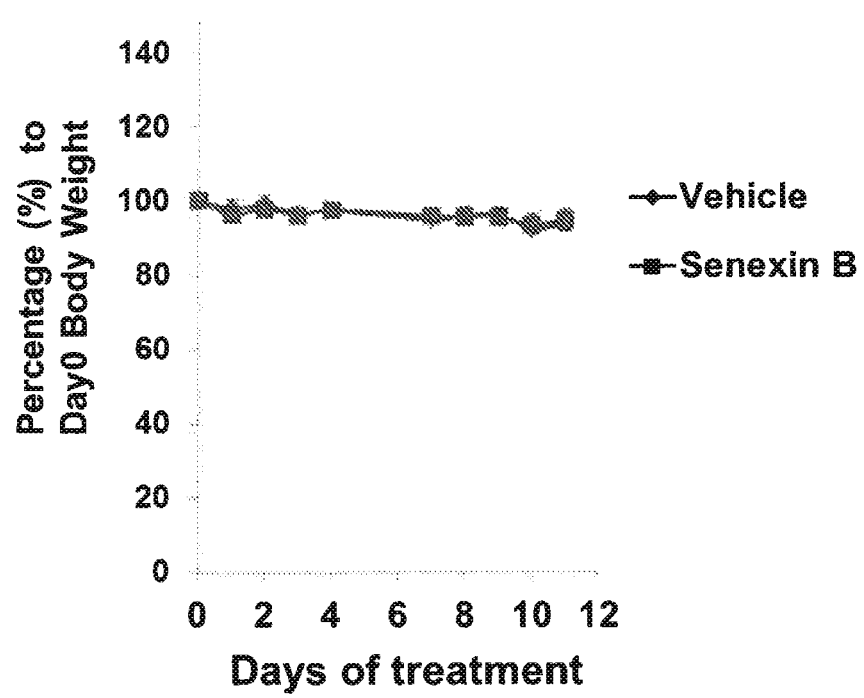
FIG. 9 shows effects of Senexin B treatment on mouse body weights.
Figure 10:
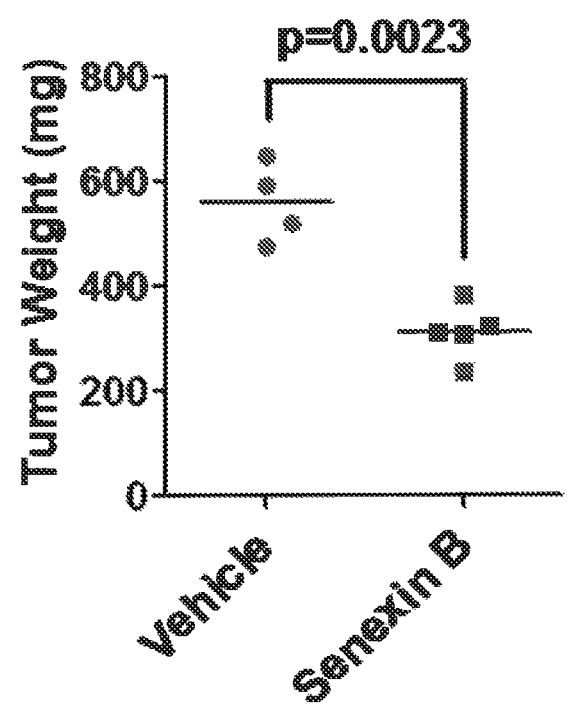
FIG. 10 shows effects of Senexin B treatment on final tumor weights.

CDK8/19 Inhibitor Senexin B Inhibits the In Vivo Xenograft Growth of LNCaP-LN3 Cells in Nude Mice 6-8 week-old nude male mice (Jackson Laboratory) were subcutaneously injected with 2 million LN-CaP LN3 (LN3) prostate cancer cells in the right flank, with Matrigel. Visible tumors formed ~14 days after injection. Mice with similar tumor volumes were then randomized into two groups and treated for 2 weeks (5 days per week) with daily i.p. injections of 40 mg/kg Senexin B or an equal volume of vehicle solution. The tumor size was measured by caliper 3 times per week and calculated by the equation length*width*width*0.5. As shown in FIG. 8, Senexin B treatment dramatically inhibits tumor growth of LN3 cells in male nude mice relative to mice treated with vehicle control. Senexin B treatment had no effects on body weight of the hosts (FIG. 9) and treated mice looked as healthy as the mice in the vehicle control group. At the end of the experiment, mice from each group were sacrificed to determine final tumor weight. As shown in FIG. 10, the weights of tumors that developed in Senexin B-treated mice were significantly lower than the weights of tumors from the control group, consistent with the difference observed from tumor volume measurement in FIG. 8. In summary, the data suggest that inhibition of CDK8/19 kinase activity would be a potential therapeutic method to block the tumor growth of advanced prostate cancer cells.

REFERENCES

1. Balk SP, Knudsen KE. AR, the cell cycle, and prostate cancer. Nucl Recept Signal 2008; 6:e001.
2. Vis AN, Schroder FH. Key targets of hormonal treatment of prostate cancer. Part 1: the androgen receptor and steroidogenic pathways. BJU Int 2009; 104:438-48.
3. Bennett NC, Gardiner RA, Hooper JD, Johnson DW, Gobe GC. Molecular cell biology of androgen receptor signalling. Int J Biochem Cell Biol 2010; 42:813-27.
4. Chng K R, Chang CW, Tan SK, et al. A transcriptional repressor co-regulatory network governing androgen response in prostate cancers. EMBO J 2012; 31:2810-23.
5. Urbanucci A, Marttila S, Janne OA, Visakorpi T. Androgen receptor overexpression alters binding dynamics of the receptor to chromatin and chromatin structure. Prostate 2012; 72:1223-32.
6. Zhu Z, Shi M, Hu W, et al. Dose-dependent effects of small-molecule antagonists on the genomic landscape of androgen receptor binding. BMC Genomics 2012; 13:355.
7. Carles J, Castellano D, Climent MA, Maroto P, Medina R, Alcaraz A. Castration-resistant metastatic prostate cancer: current status and treatment possibilities. Clin Transl Oncol 2012; 14:169-76.
8. Garcia JA, Rini BI. Castration-resistant prostate cancer: many treatments, many options, many challenges ahead. Cancer 2012; 118:2583-93.
9. Bianchini D, de Bono JS. Continued targeting of androgen receptor signalling: a rational and efficacious therapeutic strategy in metastatic castration-resistant prostate cancer. Eur J Cancer 2011; 47 Suppl 3:S189-94.
10. Ryan CJ, Tindall DJ. Androgen receptor rediscovered: the new biology and targeting the androgen receptor therapeutically. J Clin Oncol 2011; 29:3651-8.
11. Shiota M, Yokomizo A, Naito S. Increased androgen receptor transcription: a cause of castration-resistant prostate cancer and a possible therapeutic target. J Mol Endocrinol 2011; 47:R25-41.
12. Chen Y, Sawyers CL, Scher HI. Targeting the androgen receptor pathway in prostate cancer. Curr Opin Pharmacol 2008; 8:440-8.
13. Dehm SM, Tindall DJ. Alternatively spliced androgen receptor variants. Endocr Relat Cancer 2011; 18:R183-96.
14. Knudsen KE, Scher HI. Starving the addiction: new opportunities for durable suppression of AR signaling in prostate cancer. Clin Cancer Res 2009; 15:4792-8.
15. Attard G, Belldegrun AS, de Bono JS. Selective blockade of androgenic steroid synthesis by novel lyase inhibitors as a therapeutic strategy for treating metastatic prostate cancer. BJU Int 2005; 96:1241-6.
16. Ang JE, Olmos D, de Bono JS. CYP17 blockade by abiraterone: further evidence for frequent continued hormone-dependence in castration-resistant prostate cancer. Br J Cancer 2009; 100:671-5.
17. Chen Y, Clegg NJ, Scher HI. Anti-androgens and androgen-depleting therapies in prostate cancer: new agents for an established target. Lancet Oncol 2009; 10:981-91.
18. Tran C, Ouk S, Clegg NJ, et al. Development of a second-generation antiandrogen for treatment of advanced prostate cancer. Science 2009; 324:787-90.
19. de Bono JS, Logothetis CJ, Molina A, et al. Abiraterone and increased survival in metastatic prostate cancer. N Engl J Med 2011; 364:1995-2005.
20. Scher HI, Beer TM, Higano CS, et al. Antitumour activity of MDV3100 in castration-resistant prostate cancer: a phase 1-2 study. Lancet 2010; 375:1437-46.
21. Hoffman-Censits J, Fu M. Chemotherapy and targeted therapies: are we making progress in castrate-resistant prostate cancer? Semin Oncol 2013; 40:361-74.
22. Li H, Zhou H, Wang D, et al. Versatile pathway-centric approach based on high-throughput sequencing to anticancer drug discovery. Proc Natl Acad Sci USA 2012; 109:4609-14.
23. Li H, Hassona MD, Lack NA, et al. Characterization of a new class of androgen receptor antagonists with potential therapeutic application in advanced prostate cancer. Mol Cancer Ther 2013.
24. Loddick SA, Ross SJ, Thomason AG, et al. AZD3514: A Small Molecule That Modulates Androgen Receptor Signaling and Function In Vitro and In Vivo. Mol Cancer Ther 2013; 12:1715-27.
25. Cai C, He HH, Chen S, et al. Androgen receptor gene expression in prostate cancer is directly suppressed by the androgen receptor through recruitment of lysine-specific demethylase 1. Cancer Cell 2011; 20:457-71.
26. Malumbres M, Harlow E, Hunt T, et al. Cyclin-dependent kinases: a family portrait. Nat Cell Biol 2009; 11:1275-6.
27. Westerling T, Kuuluvainen E, Makela TP. Cdk8 is essential for preimplantation mouse development. Mol Cell Biol 2007; 27:6177-82.
28. Donner AJ, Ebmeier CC, Taatjes DJ, Espinosa JM. CDK8 is a positive regulator of transcriptional elongation within the serum response network. Nat Struct Mol Biol 2010; 17:194-201

29. Porter DC, Farmaki E, Altilia S, et al. CDK8 mediates chemotherapy-induced tumor-promoting paracrine activities Proc Natl Acad Sci USA 2012; 109 no. 34:13799-804.
30. Galbraith MD, Donner AJ, Espinosa JM. CDK8: A positive regulator of transcription. Transcription 2010; 1:4-12.
31. Knuesel MT, Meyer KD, Donner AJ, Espinosa JM, Taatjes DJ. The human CDK8 subcomplex is a histone kinase that requires Med12 for activity and can function independently of mediator. Mol Cell Biol 2009; 29:650-61.
32. Knuesel MT, Meyer KD, Bernecky C, Taatjes DJ. The human CDK8 subcomplex is a molecular switch that controls Mediator coactivator function. Genes Dev 2009; 23:439-51.
33. Akoulitchev S, Chuikov S, Reinberg D. TFIIH is negatively regulated by Cdk8-containing mediator complexes. Nature 2000; 407:102-6.
34. Chi Y, Huddleston MJ, Zhang X, et al. Negative regulation of Gcn4 and Msn2 transcription factors by Srb10 cyclin-dependent kinase. Genes Dev 2001; 15:1078-92.
35. Donner AJ, Szostek S, Hoover JM, Espinosa JM. CDK8 is a stimulus-specific positive coregulator of p53 target genes. Mol Cell 2007; 27:121-33.
36. Firestein R, Bass AJ, Kim SY, et al. CDK8 is a colorectal cancer oncogene that regulates beta-catenin activity. Nature 2008; 455:547-51.
37. Belakavadi M, Fondell JD. Cyclin-dependent kinase 8 positively cooperates with Mediator to promote thyroid hormone receptor-dependent transcriptional activation. Mol Cell Biol 2010; 30:2437-48.
38. Zhao X, Feng D, Wang Q, et al. Regulation of lipogenesis by cyclin-dependent kinase 8-mediated control of SREBP-1. J Clin Invest 2012; 122:2417-27.
39. Kapoor A, Goldberg MS, Cumberland LK, et al. The histone variant macroH2A suppresses melanoma progression through regulation of CDK8. Nature 2010; 468:1105-9.
40. Adler AS, McCleland ML, Truong T, et al. CDK8 Maintains Tumor Dedifferentiation and Embryonic Stem Cell Pluripotency. Cancer Res 2012; 72:2129-39.
41. Tsutsui T, Fukasawa R, Tanaka A, Hirose Y, Ohkuma Y. Identification of target genes for the CDK subunits of the Mediator complex. Genes Cells 2011.
42. Tepper CG, Boucher DL, Ryan PE, et al. Characterization of a novel androgen receptor mutation in a relapsed CWR22 prostate cancer xenograft and cell line. Cancer Res 2002; 62:6606-14.
43. Parrondo R, de las Pozas A, Reiner T, Rai P, Perez-Stable C. NF-kappaB activation enhances cell death by antimitotic drugs in human prostate cancer cells. Mol Cancer 2010; 9:182.
44. Hafeez BB, Siddiqui IA, Asim M, et al. A dietary anthocyanidin delphinidin induces apoptosis of human prostate cancer PC3 cells in vitro and in vivo: involvement of nuclear factor-kappaB signaling. Cancer Res 2008; 68:8564-72.
45. Gasparian AV, Yao YJ, Kowalczyk D, et al. The role of IKK in constitutive activation of NF-kappaB transcription factor in prostate carcinoma cells. J Cell Sci 2002; 115: 141-51.

What is claimed is:

1. A method for treating prostate cancer in a subject comprising administering to the subject an effective amount of a selective inhibitor of one or more of CDK8 and CDK19, wherein the prostate cancer is androgen independent and wherein said inhibitor inhibits increased activity of NF-κB.

2. The method according to claim 1, wherein the selective inhibitor of one or more of CDK8 or CDK19 is selected from Senexin A, Senexin B and combinations thereof.

3. The method according to claim 2, wherein the inhibitor inhibits CDK19.

4. The method according to claim 2, wherein the inhibitor inhibits CDK8.

5. The method according to claim 2, wherein the inhibitor inhibits CDK8 and CDK19.

6. The method according to claim 2, wherein the prostate cancer is androgen independent due to one or more of androgen receptor gene amplification, androgen receptor gene mutation, ligand-independent transactivation of androgen receptor and activation of intracellular androgen synthesis.

* * * * *